United States Patent [19]

Andersen et al.

[11] Patent Number: 4,594,074

[45] Date of Patent: Jun. 10, 1986

[54] NON-OCCLUDING HIGH FLOW ENTERAL FEEDING TUBE

[75] Inventors: Erik Andersen, Vernon Hills; Robert B. Edwards, II, Libertyville; David G. Quinn, Grayslake, all of Ill.

[73] Assignee: Viridian, Inc., Wheeling, Ill.

[21] Appl. No.: 731,443

[22] Filed: May 6, 1985

[51] Int. Cl.[4] .......... A61M 31/005

[52] U.S. Cl. .......... 604/270; 604/280; 604/283

[58] Field of Search .......... 604/93, 164, 266–268, 604/280–281, 283

[56] References Cited

U.S. PATENT DOCUMENTS

| | | | |
|---|---|---|---|
| 1,879,249 | 9/1932 | Honsaker | 604/280 |
| 3,881,254 | 5/1975 | Epstein | 604/268 |
| 4,270,542 | 6/1981 | Plumley | 128/350 |
| 4,381,011 | 4/1983 | Somers, III | 128/635 |
| 4,388,076 | 6/1983 | Waters | 604/165 |
| 4,390,017 | 6/1983 | Harrison et al. | 604/270 |
| 4,410,320 | 10/1983 | Dykstra et al. | 604/27 |
| 4,490,143 | 12/1984 | Quinn et al. | 604/270 |
| 4,496,347 | 1/1985 | MacLean et al. | 604/164 |
| 4,516,970 | 5/1985 | Kaufman et al. | 604/270 |
| 4,552,554 | 11/1985 | Gould et al. | 604/280 |

FOREIGN PATENT DOCUMENTS

| | | | |
|---|---|---|---|
| 0900765 | 7/1945 | France | 604/280 |
| 0745379 | 2/1956 | United Kingdom | 604/280 |

*Primary Examiner*—C. Fred Rosenbaum
*Assistant Examiner*—Michelle Lester
*Attorney, Agent, or Firm*—Wallenstein, Wagner, Hattis, Strampel & Aubel

[57] ABSTRACT

An improved, non-occluding high fluid flow enteral feeding tube including a non-collapsible bolus carried on a distal end of the tube. The bolus having at least one opening defining a tube outlet. The one opening being defined by generally vertical bolus side walls having a selected transverse sectional height ranging from a height equal to at least one-half the inner diameter of the tube to no more than a height equal to the sum of the tube inner diameter and the thickness of the tube wall. The bolus further including an upwardly inclining internal bolus floor to gradually direct fluid from the tube, through the bolus and out of the opening minimizing disturbance of fluid flow rate.

25 Claims, 12 Drawing Figures

FIG-1
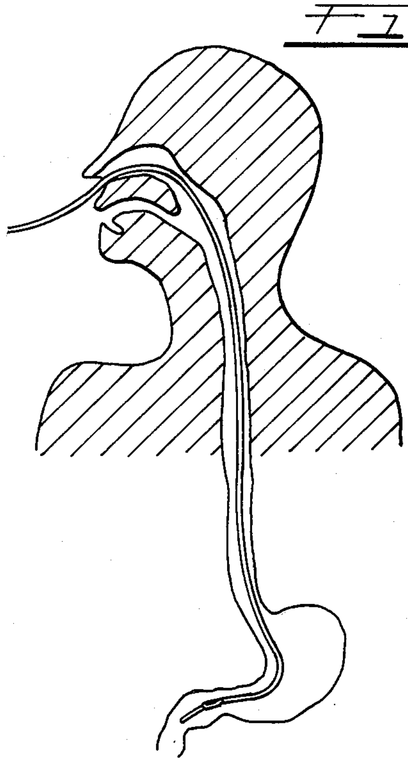
FIG-3
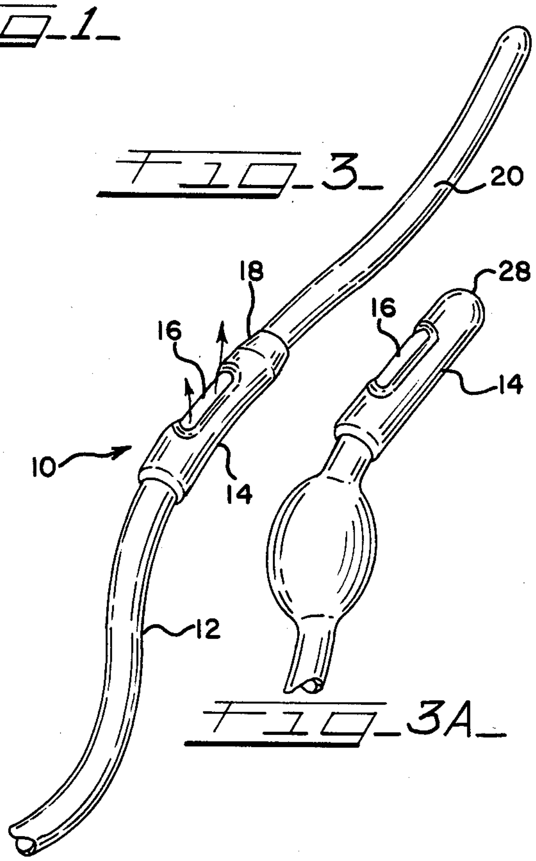
FIG-3A
FIG-4
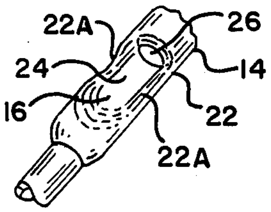
FIG-2A
PRIOR ART
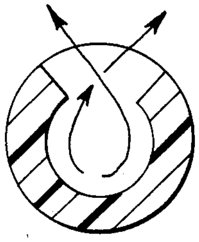
FIG-2
PRIOR ART
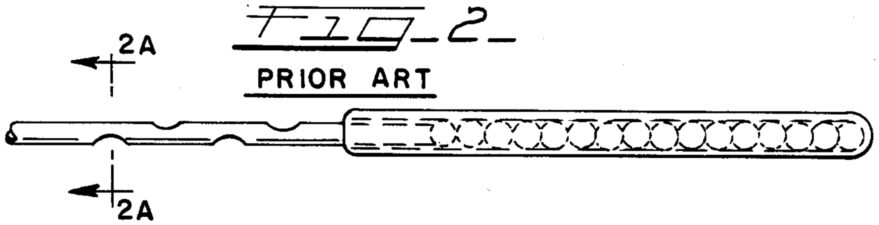

FIG. 5
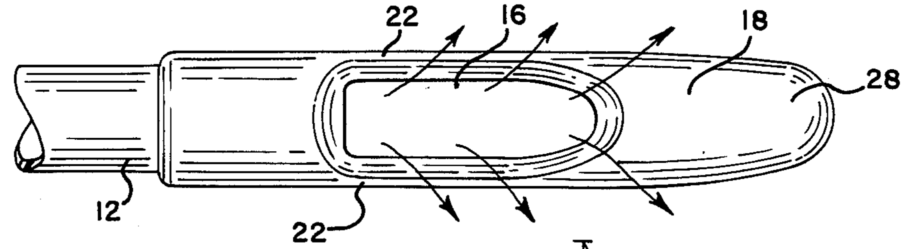
FIG. 7A
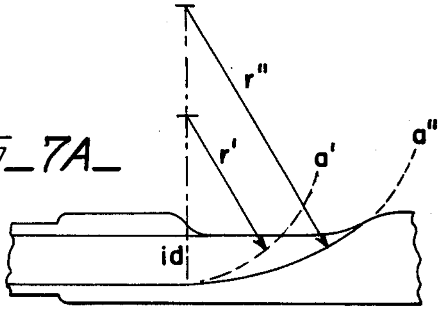
FIG. 6
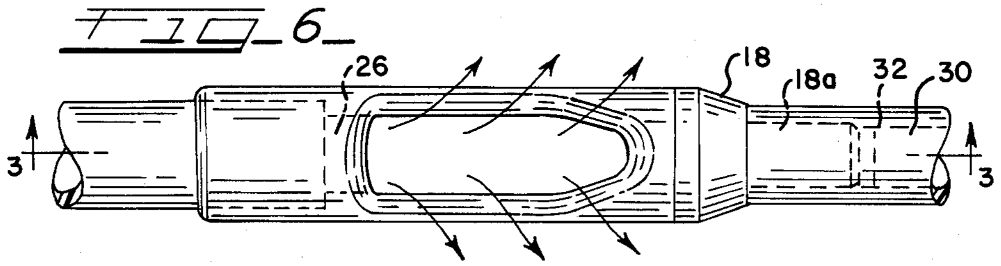
FIG. 8A
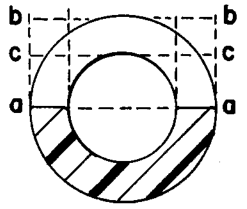
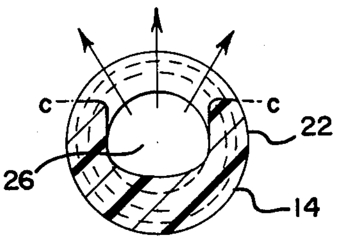
FIG. 8
FIG. 7
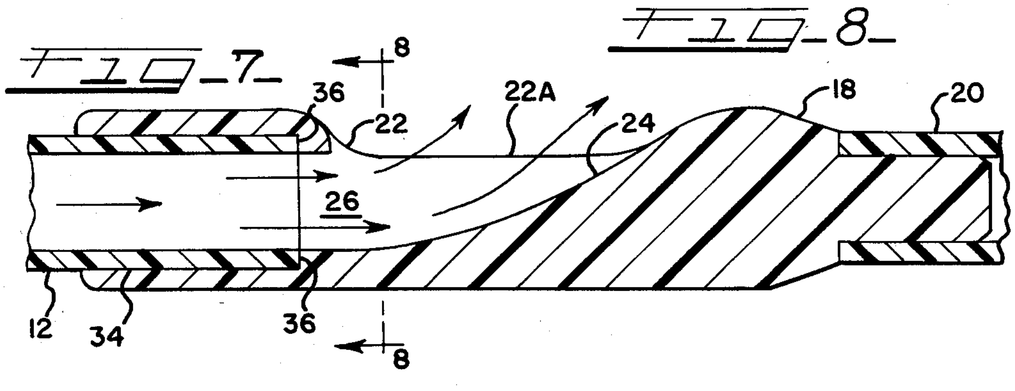

NON-OCCLUDING HIGH FLOW ENTERAL FEEDING TUBE

TECHNICAL FIELD

The present invention generally relates to the irrigation, administration and aspiration of fluids to and from body cavities such as the gastrointestinal tract through a catheter and, in particular, to an enteral feeding tube having a non-collapsible bolus containing a tube outlet disposed on a distal end of the tube.

BACKGROUND OF THE INVENTION

Enteral nutrition is a form of hyperalimentation and metabolic support in which nutrient formulas or medicaments are delivered directly to the gastrointestinal tract, either the stomach or the duodenum. Fluid administration and aspiration is accomplished through use of a nasogastrointestinal tube generally referred to as an enteral feeding tube as disclosed in FIG. 1. Enteral feeding is frequently utilized where adequate nutritional intake cannot be acheived through oral alimentation because of poor appetite, chronic nausea, general apathy, sedation or other symptoms or characteristics associated with serious disease. By delivering appropriate nutrient fluids directly to the gastrointestinal tract through an enteral feeding tube, nutritional and metabolic support of the patient is acheived without risk of sepsis or metabolic derangement as may occur in intraveneous hyperalimentation. Because of increasing emphasis on out-patient care, enteral nutrition has been recognized as a desirable method of hyperalimentation as it requires only oral intubation of the feeding tube rather than manipulation of sterile cannulae or other means of interconnection with surgically implanted subclavian catheters as used in parenteral hyperalimentation.

FIG. 2 discloses the design and configuration of a prior art enteral feeding tubes. A distal end of the feeding tube is provided with a multiplicity of tube openings through the tube side walls which define tube outlets. Distal to the tube outlets is an elongated weighted guide tip to facilitate intubation. Other examples of prior art enteral feeding tubes of similar design are disclosed in U.S. Pat. Nos. 4,410,320; 4,390,017; 4,270,542 and 4,388,076.

The disadvantages of such prior art enteral feeding tubes is the discomfort and intubation difficulties associated with initial insertion and passage of the blunt-ended guide tip into and through the naso-pharyngeal passage. Further, the patient is exposed to the risk of internal injury should a stylet exit the tube through one of the tube outlets during intubation. Further, the prior art enteral feeding tubes have an external configuration which provide no means for utilizing peristaltic action of the esophagus to assist in intubation.

As a result of such disadvantages, we developed a uniquely designed enteral feeding tube addressing the problems of prior art tubes. Our improved tubes are disclosed in U.S. Pat. No. 4,490,143 and is also the subject of a pending continuation-in-part patent application Ser. No. 614,276, filed May 25, 1984. In the enteral feeding tube disclosed therein, a non-collapsible tube insert, generally referred to as a bolus, is disposed on a distal end of the tube. The bolus carries at least one opening defining a tube outlet and has an internal passage which is normal to the tube outlet to prevent inadvertent exiting of the stylet during intubation. In addition, the bolus of our improved enteral feeding tubes further include an enlargened external configuration to utilize esophageal peristaltic action during intubation.

However, a problem encountered in all prior art enteral feeding tubes is occlusion of the tube outlet with gastrointestinal debris and cogulated feeding material which impedes administration and aspiration of fluids through the enteral feeding tube. The outlets of prior art tubes may also become blocked by being drawn up against the mucosal lining of the gastrointestinal tract during an aspiration procedure.

Another problem encountered with prior art tubes is that the tube side walls which define the tube outlets curve toward each other as disclosed in transverse section in FIG. 2A. Because of the curvature of the side walls the flow of fluid out of the tube is restricted. More importantly, the tube outlets are perpendicular to the longitudinal axis defining the fluid stream which also restricts fluid flow. None of the prior art enteral feeding tubes gradually channel the fluid stream out of the tube outlet so as to substantially maintain the same flow rate through the outlet as is present in the tube lumen. Further, the inwardly curving side walls define a tube outlet which in transverse section has a generally frustoconical shape as disclosed in FIG. 2A. Such an outlet is easily occluded with mucous and other gastrointestinal debris.

Many of the same problems discussed above are encountered with other types of catheters such as urethral and esophageal catheters.

The most preferred design of an enteral feeding tube or catheter would be an open-ended tube which would acheive maximum rate fluid flow out of the tube. Though preferable from the standpoint of maximizing fluid flow, an open-ended enteral feeding tube would be impractical. Such a tube would easily occlude with mucous during aspiration. Further, a distal end deflection tip or elongated guide tip could not be employed with an open-ended tube. Such distal end tips are necessary to guide tube passage and deflect the tube end from the mucousal linings of the gastrointestinal tract during intubation. As a result, an open-ended feeding tube could become entrapped or impaled against the mucousal linings making intubation extremely difficult and risking trauma to such tissue linings.

Hence, prior to the development of the present invention, a need existed for an enteral feeding tube which would not become occluded with feeding material or mucous. A need also existed for an enteral feeding tube having a design which would approximate the fluid flow rate characteristics of an open-ended tube and yet carry a distal end guide or deflection tip as known in the art.

SUMMARY OF THE INVENTION

According to the present invention, an enteral feeding tube has been developed utilizing a uniquely designed tube insert or bolus disposed on a distal end of the tube. The bolus contains at least one opening defining the tube outlet and has an internal design that substantially approximates the fluid flow characteristics of an open-ended tube yet does not become occluded with mucous and feeding material.

The broadest concept of the present invention utilizes a non-collapsible bolus, preferably having a generally tubular shape, with at least one opening through the bolus side wall defining a tube outlet. The bolus side walls surrounding the tube outlet are generally upright and vertical rather than arcuate as in the prior art tubes. Further, such vertical side walls are recessed to a transverse or cross-sectional height of no less than one-half the inner diameter of the tube. The bolus possess an internal passage which has an inner diameter generally equal to the inner diameter of the tube. The passage places the bolus opening in fluid communication with the tube lumen.

In addition, one end of the bolus is joined to the tube and another terminal end of the bolus is sealed. Further, the passage of the bolus has a floor which upwardly inclines from the point at which the bolus joins the tube to a distal edge of the bolus opening. The bolus floor progressively inclines so that the fluid stream is gradually channeled out of the tube without disturbance or creation of turbulance.

The transverse sectional height of the vertical side walls defining the tube outlet is one important structural feature of the enteral feeding tube of the present invention. The transverse section height of the vertical side walls may be recessed within the range of no less than one half the inner diameter of the tube to a maximum of no more than the sum of the tube inner diameter plus the cross-sectional thickness of the tube wall. In the preferred embodiment of the present invention, the transverse section of the height of the vertical side walls defining the tube outlet equals the inner diameter of the tube. Such recessed vertical side walls provides a larger tube outlet to achieve fluid flow characteristics approximating an open-ended tube. Further, such a tube outlet shape eliminates the generally frusto-conical shape of tube outlets in prior art enteral feeding tubes. By eliminating the generally frusto-conical shape and providing a larger tube outlet, the recessed vertical side walls of the bolus also prevent occlusion of the tube outlet with mucous and other gastrointestinal debris.

Another important feature of the present invention which avoids tube outlet occlusion and maximizes the rate of fluid flow is the upwardly inclining bolus floor. Preferably the incline of the bolus floor includes an upwardly curving floor in which the curvature of the floor is defined by a range of arcs circumscribed from radii having lengths proportionate to the inner diameter of the tube and related to the French size of each tube. For example, in the preferred embodiments of the present invention the length of the radius circumscribing the arc defining the curvature of the bolus floor should be between 5 times and 10 times the inner diameter of the tube. A radius with a length less than five times the inner diameter of the tube results in a curvature of the bolus floor which is too severe, thereby restricting both fluid flow and resulting in occlusion of the tube outlet. A radius having a length greater than 10 times the inner diameter of the tube results in only a slight curvature to the bolus floor which is too shallow and therefore requires an unduly long bolus capable of being easily kinked.

Because the tubing of the present invention is non-occluding, and maximizes the rate of fluid flow for purposes of both aspiration and irrigation, the bolus of the present invention may also find application in gastric, esophageal and urethral catheters as well as Foley and other retention catheters.

The present invention will be more fully described in the following detailed description with reference being made to the drawings and the claims apended thereto.

BRIEF DESCRIPTION OF THE DRAWINGS

FIG. 1 is an illustration disclosing intubation and positioning of an enteral feeding tube;

FIG. 2 is a fragmented perspective view of a prior art enteral feeding tube;

FIG. 2A is a transverse sectional view taken along line 2A—2A of FIG. 2 disclosing the curving side walls of a prior art enteral feeding tube;

FIG. 3 is a perspective view of one embodiment of the enteral feeding tube of the present invention;

FIG. 3A is a perspective view of an embodiment of the present invention showing application of the non-collapsible bolus of FIG. 5 in a retention catheter;

FIG. 4 is a detailed perspective view of one embodiment of the non-collapsible bolus of the present invention;

FIG. 5 is plan view of one embodiment of the non-collapsible bolus of the present invention disclosing a distal end spherical deflection tip;

FIG. 6 is a plan view of another embodiment of the non-collapsible bolus of the present invention disclosing the distal end elongated guide tip of FIG. 3;

FIG. 7 is a longitudinal section of the non-collapsible bolus taken along lines 7—7 of FIG. 6;

FIG. 7A is the same view of FIG. 7 and discloses a range of bolus floor curvatures within the scope of the present invention;

FIG. 8 is a transverse section of the noncollapsible bolus taken along lines 8—8 of FIG. 7; and, FIG. 8A is another transverse section of the non-collapsible bolus disclosing a range of vertical side wall heights in phantom.

DETAILED DESCRIPTION

It should also be understood that while the description is made herein with reference to an enteral feeding tube, this description is by way of example only. The principles of the present invention may be applied to all types of catheter tubes, including Foley catheters, urethral catheters, and catheters for use in gastric, esophageal, pharyngeal, nasal, intestinal, rectalcolonic, choledochal, arterial, venous, cardiac and endobronchial applications.

Referring now to the drawings, FIG. 3 discloses the enteral feeding tube of the present invention generally referenced by 10. Feeding tube 10 is generally comprised of a tube body 12, aproximal end of body 12 being joined to a fluid source for fluid administration or a syringe for aspiration. Tube body 12 is manufactured from a resilient, biocompatable plastic such as polyvinylchloride, silicone or latex. Polyurethane is preferred as it has been found to provide a larger tube lumen with less thick tube side walls and yet provides maximum strength, resistance to kink formation as well as biocompatibility and chemical resistance to the highly acidic gastric fluids found within the stomach. Preferably enteral feeding tube 10 is made radiopaque by any technique known in the art in order to assist intubation as well as ascertain positioning of the distal end of tube 10.

Joined to a terminal end of feeding tube 10 is a non-collapsible insert or bolus 14 which contains at least one opening 16 defining a tube outlet. The arrows of FIG. 3 indicate outward fluid flow through opening 16. Bolus 14 has an outer diameter at least as large as the outer diameter of tube body 12. Preferably, bolus 14 has an outer diameter only slightly larger than the outer diameter of tube 12. As a result of the slightly larger outer diameter of bolus 14, intubation of tube 10 may be assisted through use of peristaltic action of the esophagus caused by esophageal lining tissue enveloping and grasping the slightly larger outer diameter of bolus 14. In the same regard, bolus 14 has an outer configuration which is generally smooth to assist comfortable insertion and intubation. Bolus 14 preferably is also made from polyurethane but is manufactured to be more rigid than tube body 12 so as to minimize distortion of opening 16 but yet permit bolus 14, to generally bend and flex in accordance with flexing of tube body 12. Preferably bolus 14 is provided with a frustoconical distal face 18 which possesses no corners or sharp ends maximizing comfort and ease of intubation.

One embodiment of enteral feeding tube 10 includes an elongated flexible guide tip 20 joined to a distal face 18 of bolus 14. The function and construction of guide tip 20 as disclosed in FIG. 3 will be described later in greater detail.

FIG. 4 discloses the external structural detail of bolus 14. Bolus 14 preferably has a generally tubular outer shape. Opening 16 has a generally ellipsoidal edge configuration. Preferably opening 16 has a length at least one half the overall length of bolus 14. An elongated and lengthly ellipsoidal opening 16 rather than the circular or oval tube outlets in prior art tubes, functions to maximize fluid flow through opening 16 and to prevent mucosal suction during aspiration. Opening 16 is defined by vertical bolus side walls 22 which are recessed to a selected height at intermediate position 22A. Recessing the height of vertical side walls 22 enhances the flow of fluid out of opening 16 to approximate the fluid flow rate of an open-ended tube. Further, by recessing vertical side walls 22, occlusion of opening 16 by mucuos and other gastrointestinal debris is avoided.

FIG. 4 further discloses a bolus floor 24 which slopes downwardly from the distal end of the bolus to a longitudinal passage 26 contained within bolus 14. The function of downwardly curving bolus floor 24 will be discussed later in greater detail.

FIGS. 5 and 6 discloses two embodiments of bolus 14. FIG. 5 discloses an embodiment in which distal face 18 of bolus 14 carries a generally spherical deflection or "bullet" tip 28. Tip 28 may be utilized for those patients who can easily intubate tube 10 and tolerate intubation without any discomfort arising from use of spherical tip 28 during intubation.

FIG. 3A discloses one application of the "bullet" tip bolus 14 of FIG. 5 on a distal portion of a catheter, such as a retention or Foley catheter. The bolus 14 provides an opening for access to the catheter lumen yet maximizes aspiration and irrigation of fluids without occlusion of the lumen.

FIG. 6 discloses a more commonly utilized embodiment of tube 10 in which elongated guide tip 20 is disposed on distal face 18 and particularly a distal end post 18A (shown in phantom in FIG. 6) of bolus 14. As disclosed in FIG. 3, elongated guide tip 20 is generally between two and three times the length of bolus 14. FIG. 6 discloses in phantom guide tip 20 being internally weighted with a plurality of discrete weight cylinders 30, preferably made from tungsten, which are packed in end-to-end alignment within a channel 32. It has been found that tungsten is preferable to either ballbearings (as disclosed in FIG. 2) or mercury weights because tungsten provides more weight per volume than either ballbearings or mercury. Further, tungsten avoids the disposal and toxicity problems associated with mercury.

The function of guide tip 20 is to decrease discomfort associated with intubation as well as effect parting of esophageal and gastrointestinal lining tissues. The parting of such tissues is achieved since guide tip 20 preferably has an outer diameter generally smaller than the outer diameter of either bolus 14 of tube body 12. Through such smaller outer diameter, guide tip 20 permits a patient to become accustom to initial insertion of feeding tube 10 and to achieve an initial parting of gastrointestinal tissue to allow passage of the larger diametered bolus 14 and tube body 12.

In the embodiments disclosed in both FIGS. 5 and 6, spherical tip 28 as well as elongated guide tip 20 contain a water activated lubricant to facilitate intubation. Further, the same lubricant is provided within tube 10 to facilitate removal of the wire intubation stylet (not shown in the drawings) from tube 10 after intubation.

FIG. 6 also discloses in phantom a longitudinal passage 26 within bolus 10. Preferably passage 26 has an inner diameter equal to the inner diameter of tube 10 so that passage 26 is in unrestricted fluid communication with tube 10. As a result, fluid flow from tube 10 through passage 26 and out of opening 16 is unobstructed.

FIG. 7 discloses that tube body 12 connects to bolus 14 by seating within a proximal end opening 34. Opening 34 has an outer diameter equal to the outer diameter of the tube body 12 so that when body 12 seats against shoulders 36, the tube lumen is placed in unrestricted fluid communication with bolus passage 26.

FIGS. 7, 7A, 8 and 8A disclose the novel features of the enteral feeding tube of the present invention which prevent non-occlusion of the tube outlet and maximize fluid flow out of the tube to approximate the flow rate of an open-ended tube. FIG. 7 discloses vertical side walls 22 being recessed to a lower height at **22*a*. Such lower wall height extends most of the length of opening 16. FIG. 7 also discloses the bolus floor 24 upwardly inclining from passage 26 to a distal edge of opening 16. In the preferred embodiments of the present invention, floor 24 curves upwardly to gradually channel fluid from within tube 10 out of bolus 14 through opening 16**.

In prior art enteral feeding tubes, the tube outlet typically was perpendicular to the tube lumen and consequently perpendicular to the fluid stream. As a result, fluid within the lumen could not readily exit through the tube outlets. Fluid flow out of the outlets of prior art tubes resulted when peripheral portions of the fluid stream would escape, but primarily when the fluid stream would contact a surface within the tube perpendicular to the stream which would deflect fluid through the tube outlet. Such deflection of the fluid stream creates turbulence resulting in a decrease of flow rate and severely restricting fluid output. The upwardly curving bolus floor 24 does not disturb the fluid stream through deflection but rather merely channels the fluid stream through passage 26 and outward through opening 16 as indicated by the arrows in FIG. 7.

FIG. 7A discloses a range of preferred curvatures of floor 24. The curvature of floor 24 is essentially a function of the inner diameter of tube body 12 as characterized by a particular French size. The French size scale most commonly is used to describe size for medical tubing such as enteral feeding tubing, urinary drainage tubes and catheters. The French scale (hereinafter "Fr.") is disclosed and compared against the American and English medical tubing size scales in *Remington's Pharmaceutical Sciences* (6th Ed. 1980; Mack Publishing Co.) pp. 1906–1907. Generally, the enteral feeding tubing employed in the present invention have French sizes from five to ten Fr. and are generally from 15 to 42 inches in length depending on whether the medical application is for neonatal, juvenile or adult patients.

The upward curvature of the bolus floor 24 cannot be too severe otherwise obstruction of the fluid stream will result causing fluid turbulence and decreasing fluid flow output. On the other hand, the upward curvature of bolus floor 24 cannot be shallow so as to require an overly long bolus to accommodate the more gradual incline.

FIG. 7A discloses bolus floor curvatures which minimize fluid flow rates. The selected range of curvatures is defined by arcs (a) circumscribed from radii (r) having lengths of between and including five times and ten times the inner diameter of tube 10. FIG. 7A generally discloses one end of the general range of preferred bolus floor curvatures in which an arc a' is circumscribed from a radius r' having a length equal to five times the inner diameter (id) of tube body 12. At the other end of the range of preferred bolus floor curvatures, an arc a" is circumscribed from a radius r' having a length equal to ten times the id of tube body 12.

In specific embodiments of the present invention, a six French enteral feeding tube having an inner diameter of about 0.055 inches requires the radius r defining the curvature of bolus floor 24 to have a length of about 0.489 inches or 8.890 times the the inner diameter of tubing body 12. In an embodiment comprised of eight French enteral feeding tubing having an inner diameter of about 0.078 inches, the upward curvature of bolus floor 24 is defined by an arc circumscribed from a radius r having a length of 0.525 inches or 6.730 times the inner diameter of the tube body 12. In another specific embodiment of the present invention utilizing ten French enteral tubing having an inner diameter of 0.100 inches, bolus floor 24 was defined from an arc circumscribed from a radius having a length of 0.525 inches or 5.25 times the inner diameter of tube body 12.

Finally, FIGS. 8 and 8A disclose another important feature of the present invention, namely the selective recessing or lowering of the height of the vertical side walls 22 which define bolus opening 16. FIG. 8A discloses in transverse section and in solid and phantom lines, the preferred range of heights of side walls 22 at the point of lowest recess position 22A as disclosed in FIG. 7. It has been found that the transverse sectional height of vertical side walls 22 may range from a minimum height wherein side walls 22 are equal to one-half the inner diameter of tubing 10. Such minimum transverse sectional height of side walls 22 is disclosed by line A—A of FIG. 8A. Because passage 26 has the same inner diameter of tubing 10, the transverse sectional height of side walls 22 may be expressed in terms of the proportion of the inner diameter of tubing 10 even though side walls 22 surround only passage 26. At a maximum, the transverse sectional height of side walls 22 should be no greater than the sum of the inner diameter of tubing 10 plus the thickness of the walls of tube body 12. Such maximum transverse sectional height side walls 22 is disclosed by line B—B in FIG. 8A. In the preferred embodiment of the present invention, the transverse sectional height of side walls 22 is equal to about the inner diameter of tubing 10 as disclosed in FIG. 8A by line C—C and in FIG. 8.

If the transverse sectional height of side walls 22 is less than one half the inner diameter of tubing 10 then bolus 14 has an increased tendency to kink or bend. On the other hand, vertical side walls having a transverse sectional height greater than the sum of the inner diameter and thickness of tube walls 12 results in a vertical side wall height exceeding the outer configuration of bolus 14 thereby creating difficulty in intubation. It is to be understood that unlike the inwardly curving side walls of prior art tubing as disclosed in FIG. 2A or our previously patented feeding tube bolus, bolus 14 of the present invention is disclosed in FIG. 8 and includes generally vertical side walls 22 defining the opening 16 which comprises the tube outlet and with a bolus floor 24 having a selected upwardly curvature prevents and maximizes tube outlet occlusion of the rate of fluid flow out of tube 10.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to a particular embodiment disclosed as the best mode contemplated for carrying out the invention, but that the invention will include all embodiments falling within the scope of the appended claims.

I claim:

1. An enteral feeding tube for adminstration and aspiration of fluids within the gastrointestinal tract, the tube having a wall of selected thickness, a proximal end of the tube for joining to a fluid nutrient source, a distal end of the tube comprising:

a non-collapsible bolus, a proximal end of the bolus in fluid communication with the tube, a terminal end of the bolus being sealed, the bolus containing at least one opening defining a tube outlet, the bolus having an outer diameter generally at least as large as the outer diameter of the tube, the bolus further including:

(a) side walls, a portion of the side walls being lowered and upwardly facing to define the opening, the lowered side wall portions having a transverse sectional height equal to at least the inner diameter of the tube; and, (b) an upwardly curving inner bolus floor, the floor gradually channeling the fluid to the opening, the curvature of the floor being defined by an arc circumscribed from a, radius having a length equal to at least five times the inner diameter of the tube, whereby the recessed side walls and upwardly curving floor of the bolus prevent occlusion of the tube outlet and permit a fluid flow through the tube outlet substantially approximating fluid flow through an open-ended tube.

2. The enteral feeding tube of claim 1 wherein the transverse sectional height of the bolus side walls is equal to no more than the sum of the inner diameter of the tube and the thickness of tube wall.

3. The enteral feeding tube of claim 1 wherein the curvature of the floor is defined by an arc circumscribed from a radius having a length equal to no more than ten times the inner diameter of the tube.

4. The enteral feeding tube of claim 1 wherein the terminal end of the bolus has a generally spherically shaped tip.

5. The enteral feeding tube of claim 1 wherein the terminal end of the bolus carries an elongated weighted quide tip.

6. An enteral feeding tube for administration and aspiration of fluids within the gastrointestinal tract, the tube having a wall of selected thickness, a proximal end of the tube for joining to a fluid nutrient source, a distal end comprising:

a non-collapsible bolus, one end of the bolus being in fluid communication with the tube, the bolus having at least one opening defining a tube outlet, the bolus having a longitudinal passage placing the tube in fluid communication with the tube outlet, the bolus further including;

(a) side walls, a portion of the side walls being recessed and generally upwardly facing to define the opening, the recessed side wall portions having a transverse sectional height equal to at least one half the inner diameter of the tube; and, (b) the longitudinal passage having an upwardly inclining floor, the floor narrowing the longitudinal passage toward the opening, the floor inclining upwardly from a proximal end of the passage and continuing until terminating proximate to a distal end of the passage, whereby the recessed side walls and the upwardly inclining floor prevent occlusion of the tube outlet and permit fluid flow through the tube outlet substantially approximating an open-ended tube.

7. The enteral feeding tube of claim 6 wherein the incline of the floor includes an upwardly curving floor.

8. The enteral feeding tube of claim 7 wherein the the curvature of the floor is defined by an arc circumscribed from a radius having a length equal to at least five times the inner diameter of the tube.

9. The enteral feeding tube of claim 6 wherein the bolus is generally tubular.

10. The enteral feeding tube of claim 6 wherein the inner diameter of the longitudinal passage is generally equal to the inner diameter of the tube.

11. The enteral feeding tube of claim 6 wherein the length of the opening is at least one-half the length of the bolus.

12. The enteral feeding tube of claim 6 wherein the transverse sectional height of the side walls is between one-half the inner diameter of the tube and the sum of the inner diameter of the tube and thickness of the tube wall.

13. An enteral feeding tube for administration and aspiration of fluids within the gastrointestinal tract, the tube having a wall of selected thickness, a proximal end of the tube being adaptable for joining to a fluid source, a distal end of the tube comprising:

a non-collapsible bolus, one end of the bolus being joined to the tube, the bolus having side walls with at least one opening, said opening defining a tube outlet, the bolus having an internal longitudinal passage placing the tube in fluid communication with said opening, the longitudinal passage having an inner diameter equal to the inner diameter of the tube, the bolus further including;

(a) portions of the side walls being recessed and generally upright to define said opening, the recessed portions having a transverse sectional height no less than one-half the inner diameter of the passage, (b) a floor of the passage upwardly inclining from about the one end of the bolus to a distal edge of said opening, the degree of incline of the floor being selectively proportional to the inner diameter of the longitudinal passage;

whereby the recessed portions and the upwardly inclining floor prevent occlusion of said opening during the administration and aspiration of fluid and acheives a fluid flow rate characteristics through said opening approximating an open end tube.

14. The enteral feeding tube of claim 13 wherein the transverse sectional height of the recessed portions is between one-half the inner diameter of the tube and the sum of the tube inner diameter and the thickness of the tube wall.

15. The enteral feeding tube of claim 13 wherein the upward incline of the floor includes an upwardly curving of the floor.

16. The enteral feeding tube of claim 15 wherein the upward curvature of the floor is defined by an arc circumscribed from a radius having a length of no less than five times the inner diameter of the tube.

17. The enteral feeding tube of claim 16 wherein the upward curvature of the floor is defined by an arc circumscribed from a radius having a length of no more than ten times the inner diameter of the tube.

18. The enteral feeding tube of claim 17 wherein the length of the radius of the arc defining the curvature of the floor for a 10 French tube is 5.250 times the inner diameter of the tube.

19. The enteral feeding tube of claim 17 wherein the length of the radius of the arc defining the curvature of the floor for an 8 French tube is 6.730 times the inner diameter of the tube.

20. The enteral feeding tube of claim 17 wherein the length of the radius of the arc defining the curvature of the floor for a 6 French tube is 8.890 times the inner diameter of the tube.

21. In an enteral feeding tube for administration and aspiration of fluids within the gastrointestinal tract, a proximal end of the tube being joined to a fluid nutrient source, a distal end of the tube being joined to a non-collapsible bolus, the bolus having an internal longitudinal passage in fluid communication with the tube, the bolus having side walls with at least one opening in the side walls defining a tube outlet, the improvement comprising:

(a) the length of the one opening being generally about one half the length of the bolus;

(b) the bolus side walls defining the one opening having a lowered height and being generally vertical, the side walls having a transverse sectional height of between one half the tube inner diameter and the sum of the tube inner diameter and tube wall thickness; and, (c) an upwardly curving bolus floor, the floor narrowing the passage to the one opening, the curvature of the floor being defined by an arc having a radius with a length between at least five times the inner diameter of the tube and ten times the inner diameter of the tube, such that the generally vertical side walls and the upwardly curving floor of the bolus prevents occlusion of the tube outlet, the length of the one opening prevents suction into the bolus of mucousal tissue during aspiration and the flow of fluid through the tube outlet substantially approximates fluid flow through an open-ended tube.

22. The enteral feeding tube of claim 21 wherein the transverse height of the side walls is equal to the inner diameter of the tube.

23. The enteral feeding tube of claim 22 wherein the bolus includes a terminal end having a generally spherical shaped tip.

24. The enteral feeding tube of claim 22 wherein the bolus includes a terminal end carrying an elongated guide tip.

25. A catheter for irrigation and aspiration of fluids within body cavities, the catheter having a wall of selected thickness and a proximal end for joining to a fluid or suction source, a lower most distal end of the catheter comprising:

a non-collapsible bolus, a proximal end of the bolus in fluid communication with the catheter, a terminal end of the bolus being sealed, the bolus containing at least one opening defining a catheter outlet, the bolus having an outer diameter generally at least as large as the outer diameter of the catheter, the bolus further including:

(a) side walls, a portion of the side walls being lowered and upwardly facing to define the opening, the lowered side wall portions having a transverse sectional height equal to the inner diameter of the catheter; and, (b) an upwardly curving inner bolus floor, the floor gradually channeling the fluid to the opening, the curvature of the floor being defined by an arc circumscribed from a radius having a length equal to at least five times the inner diameter of the catheter, whereby the recessed side walls and upwardly curving floor of the bolus prevent occlusion of the catheter outlet and permits a fluid flow through the tube outlet substantially approximating fluid flow through an open-ended tube.

* * * * *

UNITED STATES PATENT AND TRADEMARK OFFICE

CERTIFICATE OF CORRECTION

PATENT NO. : 4,594,074

DATED : June 10, 1986

INVENTOR(S) : Erik Andersen, Robert B. Edwards II and David G. Quinn

It is certified that error appears in the above-identified patent and that said Letters Patent is hereby corrected as shown below:

Col. 7, lines 15 and 16, the word "minimize" bridging such lines should be --maximize--.

Col. 7, line 25, delete "r'" and insert therefor --r"--.

Col. 7, line 31, delete "the the" and insert therefor --the--.

Col. 8, line 32, delete "I" and insert therefor --We--.

Col. 8, Claim 1, line 54, delete ",".

Col. 9, Claim 5, line 6, delete "quide" and insert therefor --guide--.

Col. 9, Claim 8, line 35, delete "the the" and insert therefor --the--.

Signed and Sealed this

Twenty-fifth Day of July, 1989

Attest:

DONALD J. QUIGG

Attesting Officer

Commissioner of Patents and Trademarks